(12) United States Patent
Liu et al.

(10) Patent No.: US 12,138,119 B2
(45) Date of Patent: Nov. 12, 2024

(54) PORTABLE TELEOPERATION HAND-HELD DEVICES FOR REMOTE ULTRASOUND EXAMINATION

(71) Applicant: HEFEI HEBIN INTELLIGENT ROBOTS CO., LTD., Anhui (CN)

(72) Inventors: Zhen Liu, Hefei (CN); Dongliang Cheng, Hefei (CN)

(73) Assignee: HEFEI HEBIN INTELLIGENT ROBOTS CO., LTD., Hefei (CN)

( * ) Notice: Subject to any disclaimer, the term of this patent is extended or adjusted under 35 U.S.C. 154(b) by 0 days.

(21) Appl. No.: 18/424,851

(22) Filed: Jan. 28, 2024

(65) Prior Publication Data

US 2024/0164749 A1 May 23, 2024

Related U.S. Application Data

(63) Continuation-in-part of application No. PCT/CN2022/117693, filed on Sep. 8, 2022.

(30) Foreign Application Priority Data

Oct. 14, 2021 (CN) .......................... 202111197455.3

(51) Int. Cl.
*A61B 8/00* (2006.01)

(52) U.S. Cl.
CPC .......... *A61B 8/4427* (2013.01); *A61B 8/4218* (2013.01); *A61B 8/46* (2013.01); *A61B 8/56* (2013.01)

(58) Field of Classification Search
CPC ........... A61B 8/46; A61B 34/35; A61B 34/37; A61B 5/7455; A61B 8/44
See application file for complete search history.

(56) References Cited

U.S. PATENT DOCUMENTS

| 6,425,865 B1 | 7/2002 | Salcudean et al. |
| 2005/0183532 A1* | 8/2005 | Najafi ................. B25J 17/0266 74/490.01 |

(Continued)

FOREIGN PATENT DOCUMENTS

| CN | 207202885 U | 4/2018 |
| CN | 108065959 A | 5/2018 |

(Continued)

OTHER PUBLICATIONS

First Office Action in Chinese Application No. 202111197455.3 mailed on Oct. 10, 2022, 15 pages.

(Continued)

*Primary Examiner* — Angela M Hoffa
*Assistant Examiner* — Younhee Choi
(74) *Attorney, Agent, or Firm* — PORUS IP LLC (57) ABSTRACT

A portable teleoperation hand-held device for remote ultrasound examination is disclosed. The portable teleoperation hand-held device includes a housing, a velocity collection module disposed on the housing, an angular velocity collection module disposed on the housing, a force collection module disposed on the housing, a data processing module disposed on the housing, a pressing module disposed on the housing, and a force feedback module disposed on the housing. The velocity collection module, the angular velocity collection module, and the force collection module may be all connected to the data processing module, and respectively sends the velocity information of the hand-held device moving on the working surface, the angular velocity information of the hand-held device rotating in space, and the pressing force of the hand-held device to the data processing module, to realize a remote control of the sub-terminal scanning examination robot.

6 Claims, 7 Drawing Sheets

(56) References Cited

U.S. PATENT DOCUMENTS

| | | |
|---|---|---|
| 2010/0041991 A1 | 2/2010 | Roundhill |
| 2011/0152690 A1 | 6/2011 | Anthony et al. |
| 2015/0366546 A1 | 12/2015 | Kamen et al. |
| 2016/0104393 A1* | 4/2016 | Savitsky .............. G09B 23/285 434/262 |
| 2020/0215691 A1 | 7/2020 | Saruta et al. |
| 2021/0315545 A1* | 10/2021 | Sugiyama ................ A61B 8/46 |

FOREIGN PATENT DOCUMENTS

| | | | | |
|---|---|---|---|---|
| CN | 108994861 A | | 12/2018 | |
| CN | 209004045 U | | 6/2019 | |
| CN | 110916801 A | | 3/2020 | |
| CN | 110993087 A | * | 4/2020 | .............. A61B 8/54 |
| CN | 113180738 A | * | 7/2021 | |
| CN | 113288204 A | | 8/2021 | |
| EP | 4306056 A1 | | 1/2024 | |
| JP | H06195127 A | | 7/1994 | |

OTHER PUBLICATIONS

The Second Office Action in Chinese Application No. 202111197455.3 mailed on Jan. 28, 2023, 18 pages.
Rejection Decision in Chinese Application No. 202111197455.3 mailed on Apr. 21, 2023, 17 pages.
Decision to grant a patent in Chinese Application No. 202111197455.3 mailed on Jun. 21, 2023, 5 pages.
International Search Report in PCT/CN2022/117693 mailed on Nov. 17, 2022, 6 pages.
Written Opinion in PCT/CN2022/117693 mailed on Nov. 17, 2022, 5 pages.

* cited by examiner

PORTABLE TELEOPERATION HAND-HELD DEVICES FOR REMOTE ULTRASOUND EXAMINATION

CROSS-REFERENCE TO RELATED APPLICATIONS

This application is a continuation-in-part of International Patent Application No. PCT/CN2022/117693, filed on Sep. 8, 2022, which claims priority to Chinese Patent Application No. 202111197455.3 filed on Oct. 14, 2021, the entire contents of each of which are incorporated herein by reference.

TECHNICAL FIELD

The present disclosure relates to the field of remote ultrasound technology, and in particular to portable teleoperation hand-held devices for remote ultrasound examinations.

BACKGROUND

As the development of medical technology, ultrasound examination technology has been increasingly used in hospitals for its simplicity, portability, low cost and lack of side effects. However, due to the uneven distribution of economic development and high-quality medical resources, people in many areas are not yet able to take high-quality ultrasound examinations. The ultrasound diagnosis is achieved through a more dependable approach involves utilizing remote shared ultrasound device. However, existing remote ultrasound examination devices have complex and cumbersome structures, need a lot of auxiliary equipment to operate, and are inconvenient to carry and install.

Therefore, a portable teleoperation hand-held device for remote ultrasound examination is needed, which is convenient to carry and install. An examination robot is configured at a patient's end, and a doctor remotely controls the examination robot to perform ultrasound diagnosis to realize a sharing of resources, which may solve a shortage of resources in remote areas and grassroots areas.

SUMMARY

Some embodiments of the present disclosure provide a portable teleoperation hand-held device for remote ultrasound examination. The portable teleoperation hand-held device may include a housing, a velocity collection module disposed on the housing, an angular velocity collection module disposed on the housing, a force collection module disposed on the housing, a data processing module disposed on the housing, a pressing module disposed on the housing, and a force feedback module disposed on the housing. The velocity collection module may be configured to obtain velocity information of the hand-held device moving on a working surface. The angular velocity collection module may be configured to obtain angular velocity information of the hand-held device rotating in space. The force collection module may be connected to the pressing module, and may be configured to obtain a pressing force to which the pressing module may be subjected, the pressing force to which the pressing module may be subjected being a pressing force of the hand-held device. The velocity collection module, the angular velocity collection module, and the force collection module may be all connected to the data processing module, and respectively send the velocity information of the hand-held device moving on the working surface, the angular velocity information of the hand-held device rotating in space, and the pressing force of the hand-held device to the data processing module, to realize a remote control of the sub-terminal scanning examination robot. The data processing module may be further configured to receive a contact force between an ultrasound probe on an end of the sub-terminal scanning examination robot and a scanning portion of a human body, i.e., to receive an actual contact force of the ultrasound probe, and send the actual contact force of the ultrasound probe to the force feedback module. The force feedback module may be configured to provide real-time feedback on the actual contact force of the ultrasound probe. The hand-held device may be move on the working surface, and the working surface may be any working surface. The hand-held device may be an imitation ultrasound probe, the pressing module may be an end cover disposed on one end of the housing, and an outer surface of the end cover may be a pressing surface of the hand-held device. The velocity collection module may adopt a photoelectric velocity sensor and may be disposed in the housing. A velocity detection window may be opened on the outer surface of the end cover, i.e., on the pressing surface of the hand-held device, and a photoelectric detecting end of the photoelectric velocity sensor may perform a photoelectric detection through the velocity detection window to obtain the velocity information of the hand-held device moving on the working surface. The force feedback module may include a display. The display may be connected to the data processing module to obtain the pressing force of the hand-held device and the actual contact force of the ultrasound probe. The display may be configured to display in real time the pressing force of the hand-held device, the actual contact force of the ultrasound probe, and a difference between the pressing force of the hand-held device and the actual contact force of the ultrasound probe. The force feedback module may further include a vibration module. The vibration module may be connected to the data processing module to obtain the difference between the pressing force of the hand-held device and the actual contact force of the ultrasound probe. The vibration module may be configured to generate a vibration according to the difference, if the difference may be greater than a certain set threshold, the vibration module generates the vibration, and the greater the difference is, the greater a vibration intensity of the vibration may be.

BRIEF DESCRIPTION OF THE DRAWINGS

The present disclosure is further illustrated in terms of exemplary embodiments, and these exemplary embodiments are described in detail with reference to the drawings. These embodiments are not limiting. In these embodiments, the same number indicates the same structure, wherein.

DETAILED DESCRIPTION

In order to illustrate the technical solutions related to the embodiments of the present disclosure, a brief introduction of the drawings referred to in the description of the embodiments is provided below. Obviously, the drawings described below are only some examples or embodiments of the present disclosure. Those skilled in the art, without further creative efforts, may apply the present disclosure to other similar scenarios according to these drawings. Unless apparent from the locale or otherwise stated, like reference numerals represent same structures or operations throughout the several views of the drawings.

The flowcharts used in the present disclosure illustrate operations that systems implement according to some embodiments in the present disclosure. It is to be expressly understood, the operations of the flowchart may be implemented not in order. Conversely, the operations may be implemented in an inverted order, or simultaneously. Moreover, one or more other operations may be added to the flowcharts. One or more operations may be removed from the flowcharts.

Figure 1:
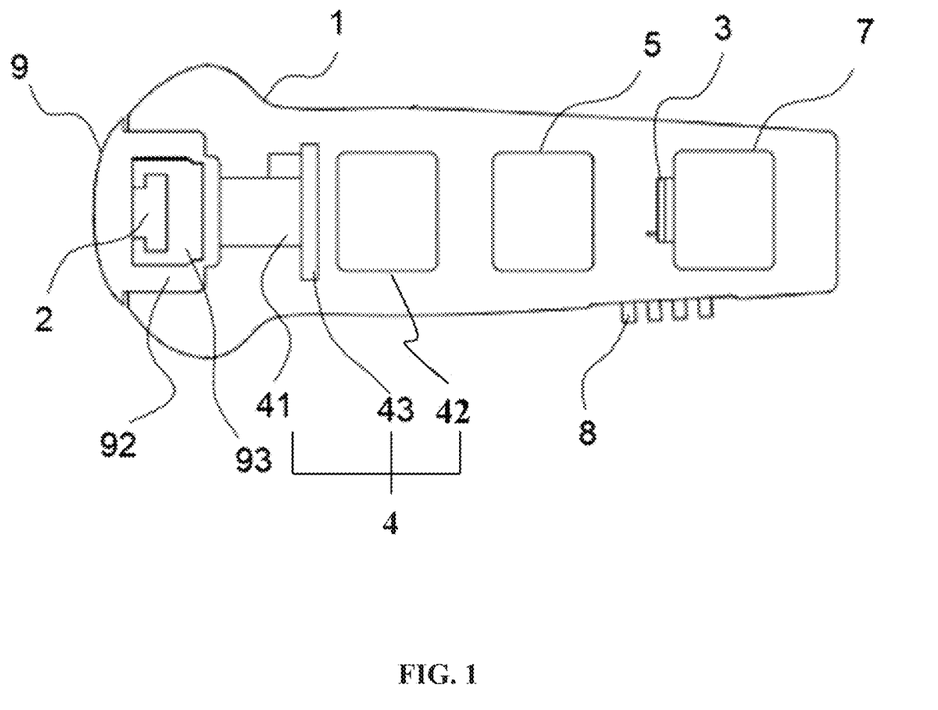
FIG. 1 illustrates a schematic diagram of an internal structure of a hand-held device of the present disclosure according to some embodiments of the present disclosure.
Figure 2:
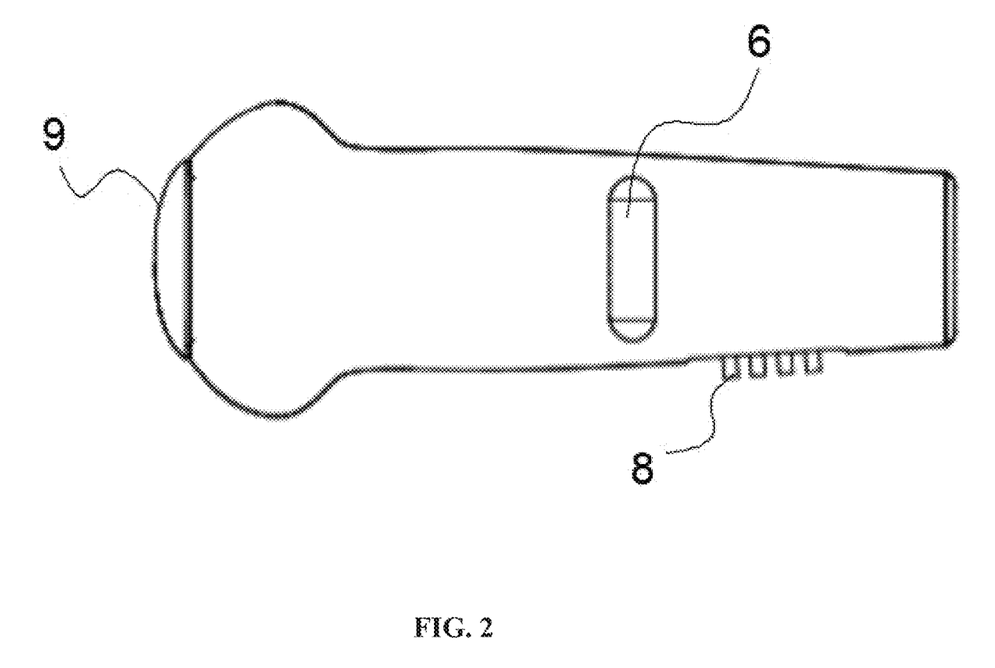
FIG. 2 illustrates an external schematic diagram of a hand-held device of the present disclosure according to some embodiments of the present disclosure.

FIG. 1 illustrates a schematic diagram of an internal structure of a hand-held device of the present disclosure according to some embodiments of the present disclosure. FIG. 2 illustrates an external schematic diagram of a hand-held device of the present disclosure according to some embodiments of the present disclosure.

In some embodiments, as shown in FIG. 1 and FIG. 2, a portable teleoperation hand-held device for remote ultrasound examination includes a housing 1, a velocity collection module 2, an angular velocity collection module 3, a force collection module 4, a vibration module 5, a display 6, a data processing module 7, a control module 8, and a pressing module, provided on the housing 1. The vibration module 5 and the display 6 form a force feedback module of the hand-held device.

The hand-held device is an imitating ultrasound probe. The pressing module is an end cover 9 disposed on one end of the housing 1, and an outer surface of the end cover 9 is a pressing surface of the hand-held device, a velocity detection window 91 is opened on the end cover 9. In some embodiments, the hand-held device is moved on a working surface. The working surface refers to a surface where the hand-held device works. In some embodiments, the working surface includes a flexible face and a rigid face. The flexible face includes but is not limited to a human skin model surface, a human skin surface, and a mouse pad, etc. The rigid face includes but is not limited to a rigid surface, a rigid flat face, a rigid curved face, etc.

The velocity collection module 2 refers to a function module configured to collect velocity information of the hand-held device. In some embodiments, the velocity collection module 2 adopts a photoelectric velocity sensor and is disposed in the housing 1, and a photoelectric detection end of the velocity collection module 2 is aligned with the velocity detection window 91, so that a photoelectric detection is performed through the velocity detection window 91 to obtain velocity information the hand-held device moving on a working surface. In some embodiment, the velocity information includes, but is not limited to an average velocity and an acceleration moving on the working surface.

The angular velocity collection module 3 refers to a function module configured to collect angular velocity information of the hand-held device. The angular velocity collection module 3 adopts a posture angular velocity sensor and is disposed in the housing 1. The angular velocity collection module 3 is configured to obtain angular velocity information of the hand-held device rotating in space, i.e., obtain the angular velocity information of the hand-held device rotating around three axes x, y, and z in space. Axes x and y form a horizontal plane and an axis z is a vertical direction perpendicular to the horizontal plane, and the velocity information of the hand-held device moving on the working surface includes the velocity information on the axis x and the velocity information on the axis y.

The force collection module 4 refers to a function module configured to collect force-related information of the hand-held device. The force collection module 4 is connected to the end cover 9 and is configured to collect a pressing force to which an outer surface of the end cover 9 (i.e., the pressing surface of the hand-held device) is subjected, that is, the force collection module 4 is configured to obtain the pressing force of the hand-held device.

The data processing module 7 refers to a function module configured to process the velocity information, the angular velocity information, and the pressing force. In some embodiments, the velocity collection module 2, the angular velocity collection module 3, and the force collection module 4 are all connected to the data processing module 7, which respectively sends the velocity information of the hand-held device moving on the working surface, the angular velocity information of the hand-held device rotating in space, and the pressing force of the hand-held device to the data processing module 7.

In some embodiments, the data processing module 7 is connected to a main computer by wired communication or wireless communication, and the main computer is connected to the sub-terminal scanning examination robot by 5G communication.

In some embodiments, the data processing module 7 sends the velocity information of the hand-held device moving on the working surface, the angular velocity information of the hand-held device rotating in space and the pressing force of the hand-held device to the sub-terminal scanning examination robot through the main computer. An end-effector is an assembly configured to response to a remote control instruction of the hand-held device. The remote control instruction refers to an instruction configured to remotely control the sub-terminal scanning examination robot. In some embodiments, the end-effector of the sub-terminal scanning examination robot moves according to the velocity information of the hand-held device moving on the working surface and the angular velocity information of the hand-held device rotating in space and the pressing force of the hand-held device, thereby realizing a remote control of the hand-held device to the sub-terminal scanning examination robot, which is described specifically as follows.

Exemplarily, the hand-held device controls a movement of the end-effector of the sub-terminal scanning examination robot in a horizontal plane using the velocity information of the hand-held device moving on the working surface, so that a velocity of an end of the ultrasound probe of the sub-terminal scanning examination robot moving in the horizontal plane is the same as a velocity of the hand-held device moving on the working surface.

Exemplarily, the hand-held device controls a posture movement of the end-effector of the sub-terminal scanning examination robot in the horizontal plane using the angular velocity information of the hand-held device rotating in space, so that an angular velocity of the end-effector of the sub-terminal scanning examination robot rotating in space is the same as an angular velocity of the hand-held device rotating in space.

Exemplarily, the hand-held device controls the end-effector of the sub-terminal scanning examination robot to move along a normal direction of a scanning surface using the pressing force, so that a contact force between the ultrasound probe on an end of the sub-terminal scanning examination robot and a scanning portion of the human body, i.e. an actual contact force of the ultrasound probe, reaches the pressing force of the hand-held device;

Exemplarily, the hand-held device is further configured to control the end-effector of the sub-terminal scanning examination robot to move a set distance upward or downward along the normal direction of the scanning surface. The scanning surface refers to a scanning surface of the ultrasound probe on the end of the sub-terminal scanning examination robot when the scanning portion of the human body is scanned, and the normal direction of the scanning surface is a direction perpendicular to the scanning surface.

In some embodiments, the data processing module 7 further receives the contact force between the ultrasound probe on the end of the sub-terminal scanning examination robot and the scanning portion of the human body, i.e., receives the actual contact force of the ultrasound probe.

In some embodiments, the vibration module 5 and the display 6 form a force feedback module of the hand-held device. The force feedback module is configured to provide real-time feedback on the actual contact force of the ultrasound probe.

In some embodiments, the display 6 is connected to the data processing module 7 to obtain the pressing force of the hand-held device and the actual contact force of the ultrasound probe. The display 6 is configured to display in real time the pressing force of the hand-held device, the actual contact force of the ultrasound probe, and a difference between the pressing force of the hand-held device and the actual contact force of the ultrasound probe.

In some embodiments, the real-time display of the pressing force, the actual contact force, and the difference between the pressing force and the actual contact force on the display 6 allows a doctor to more intuitively observe the two forces, and facilitates the doctor to clearly know the difference between the two forces, thereby knowing a tracking error of the actual contact force on the pressing force, and obtaining a force feedback, which facilitates the doctor to adjust the pressing force of the hand-held device 1 timely.

In some embodiments, the vibration module 5 is connected to the data processing module 7 to obtain the difference between the pressing force of the hand-held device and the actual contact force of the ultrasound probe. The vibration module 5 is configured to generate a vibration according to the difference, and if the difference is greater than a certain set threshold, the vibration module 5 generates the vibration and the greater the difference is, the greater a vibration intensity of the vibration is.

In some embodiment, the vibration module 5 generates the vibration of different integrities according to the difference between the pressing force of the hand-held device and the actual contact force of the ultrasound probe, and forms force feedback, which facilitates the doctor to timely adjust the pressing force of the hand-held device 1.

In some embodiments, the control module 8 is configured to control an ultrasound imaging and perform a mode selection, the mode selection includes a force control mode, a posture control mode, and an up-down movement control mode. The control module 8 is connected to the data processing module 7, the control module 8 sends a selected mode to the data processing module 7, and the data processing module 7 sends the selected mode to the sub-terminal scanning examination robot through the main computer to control the end-effector of the sub-terminal scanning examination robot to move in the selected mode.

Specifically, in the force control mode, the end-effector of the sub-terminal scanning examination robot is controlled to move automatically along the normal direction of the scanning surface, so that the contact force between the ultrasound probe on the end of the sub-terminal scanning examination robot and the scanning portion of the human body, i.e., the actual contact force of the ultrasound probe reaches to the pressing force of the hand-held device. In the posture control mode, the posture movement of the end-effector of the sub-terminal scanning examination robot in space is controlled, so that an angular velocity of the end-effector of the sub-terminal scanning examination robot rotating in space is the same as an angular velocity of the hand-held device rotating in space; and in the up-down movement control mode, the end-effector of the sub-terminal scanning examination robot is controlled to move a set distance along the normal direction of the scanning surface.

Figure 3:
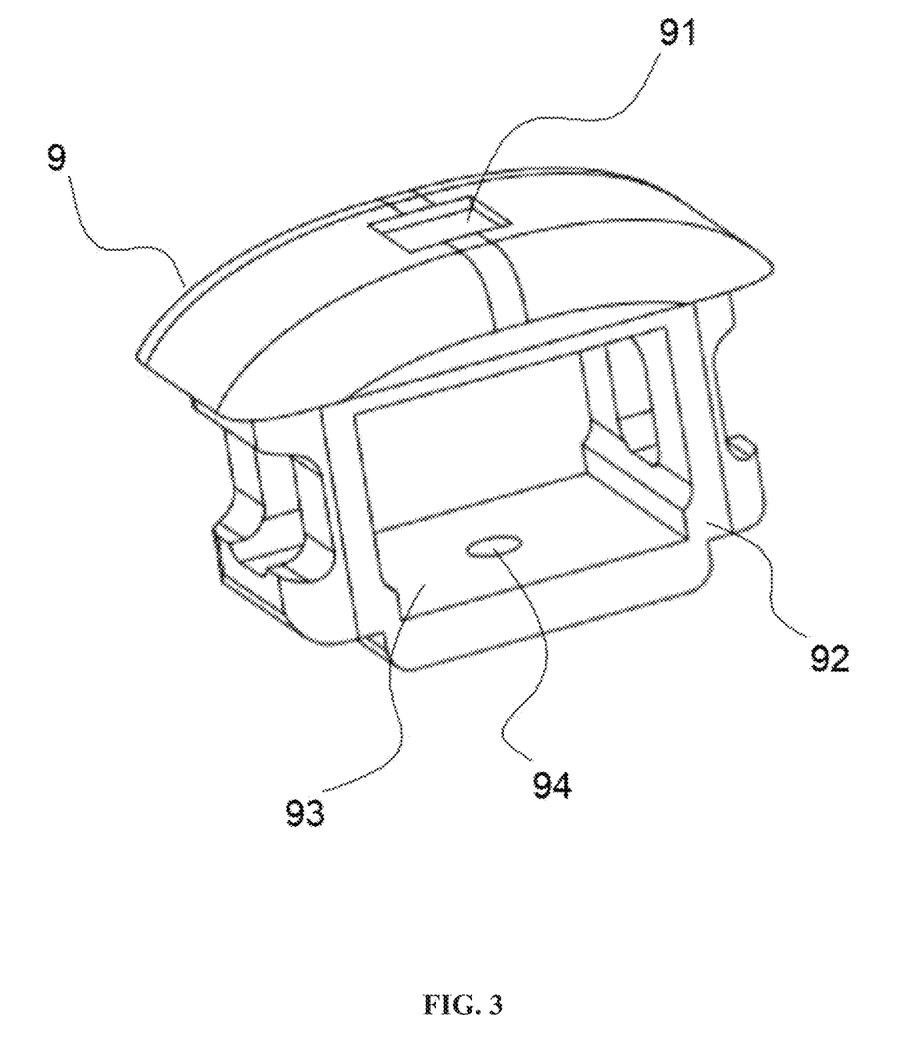
FIG. 3 illustrates a schematic diagram of an end cover of a hand-held device according to some embodiments of the present disclosure.

FIG. 3 illustrates a schematic diagram of an end cover of a hand-held device according to some embodiments of the present disclosure.

In some embodiments, as shown in FIG. 3, an outer surface of the end cover 9 is the pressing surface of the hand-held device, the pressing surface is a raised circular arc surface, and the velocity detection window 91 is opened on the raised circular arc surface. An inner surface of the end cover 9 is provided with a load-bearing connector 92. The load-bearing connector 92 is provided with a velocity collection module 2. The velocity collection module 2 is disposed in a fixing slot 93 of the photoelectric velocity sensor, and the velocity collection module 2 is aligned with the velocity detection window 91 for collecting the velocity of the hand-held device moving on the working surface and sending the velocity of the movement to the data processing module 7.

In some embodiments, as shown in FIG. 1 and FIG. 3, the force collection module 4 includes a force sensor 41 and a data transmitter 42. The force sensor 41 is fixed to a force sensor fixing plate 43 disposed in the housing 1. In some embodiments, an end of the force sensor 41 bearing force is fixedly connected or detachably connected to the inner surface of the end cover 9, candidate the specific connection manner is not limited herein. Exemplarily, a bottom surface (i.e., a side surface far away of the force-bearing connector 92 from the inner surface of the end cover 9) of the load-bearing connector 92 inside the end cover 9, is opened with a bolt hole 94. The end of the force sensor 41 bearing force is fixed to a bolt on the bottom surface of the force-bearing connector 92 through the bolt hole 94. In some embodiments, the force sensor 41 is subjected by the pressure to generate a deformation. An output end of the force sensor 41 is connected to the data transmitter 42. The data transmitter 42 is configured to perform a data processing of the deformation generated by the force sensor 41 to convert the deformation into a voltage signal, and send the voltage signal to the data processing module 7 for data processing. The data processing module 7 converts the voltage signal into a pressure value to obtain the pressing force to which the outer surface of the end cover 9 is subjected, and send the pressing force to the data processing module 7.

In some embodiments, the angular velocity collection module 3 is fixed to an angular velocity collection module fixing plate disposed in the housing 1 by a nut to ensure that when the hand-held device is rotated in space, the angular velocity collection module is capable of smoothly collecting the angular velocity information of the hand-held device rotating around the axes x, y, and z in space, and send the angular velocity information to the data processing module 7.

In some embodiments, the vibration module 5 is fixed in the housing 1 through a bolt.

In some embodiments, the display 6 is a liquid crystal display. A display window is disposed on a side wall of the housing 1, and the display 6 is disposed in a display window on the side wall of the housing 1.

In some embodiments, the control module 8 performs a mode selection using keys including a force control key, a posture control key, or an up-down movement control key. The side wall of the housing 1 is further provided with a key window, and the control module 8 is disposed in the key window on the side wall of the housing 1.

In some embodiments, the data processing module 7 adopts a microcontroller, and the data processing module 7, i.e., the microcontroller, is installed in the housing 1 through a fixed slot for preventing an upward and downward movement and a shaking of the microcontroller.

The data processing module 7 is connected to the main computer by wired connection or wireless connection. For example, the data processing module is connected to the main computer through USB, serial port, Bluetooth, WIFI connection, etc.

Figure 4:
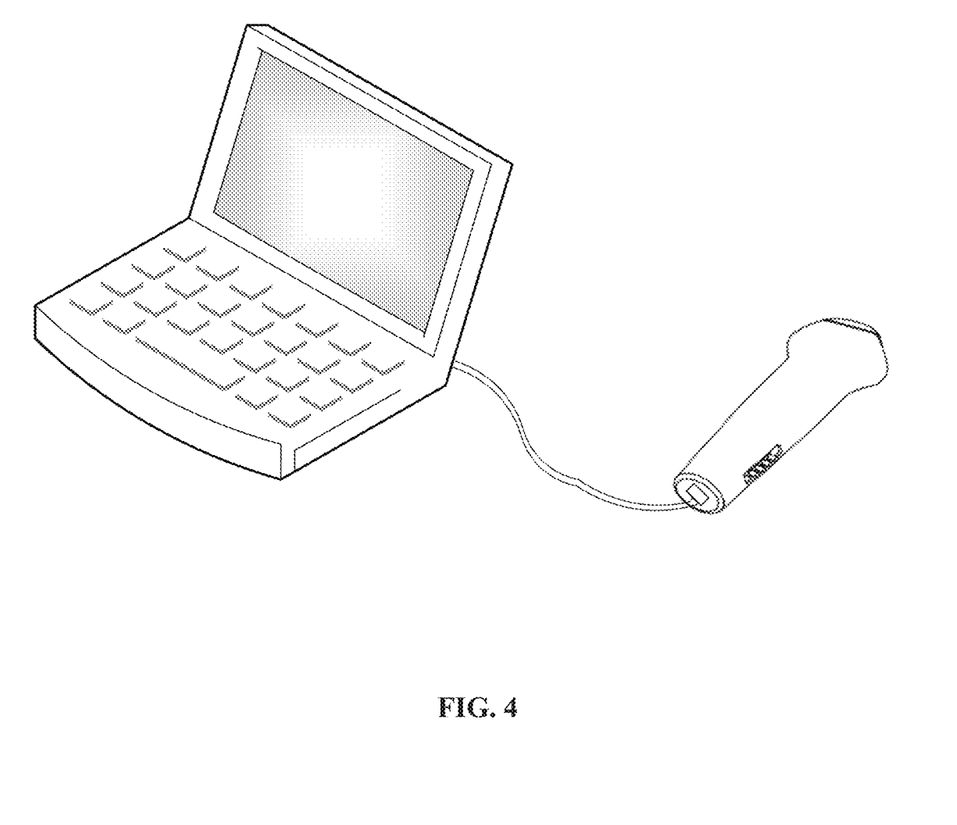
FIG. 4 illustrates a schematic diagram of a connection between a hand-held device and a main computer according to some embodiments of the present disclosure.

FIG. 4 illustrates a schematic diagram of a connection between a hand-held device and a main computer according to some embodiments of the present disclosure.

In some embodiments, as shown in FIG. 4, the hand-held device is provided with a USB interface, and the data processing module 7 transmits data by connecting the USB interface and the main computer. The hand-held device further uses the USB interface for power supply.

Figure 5:
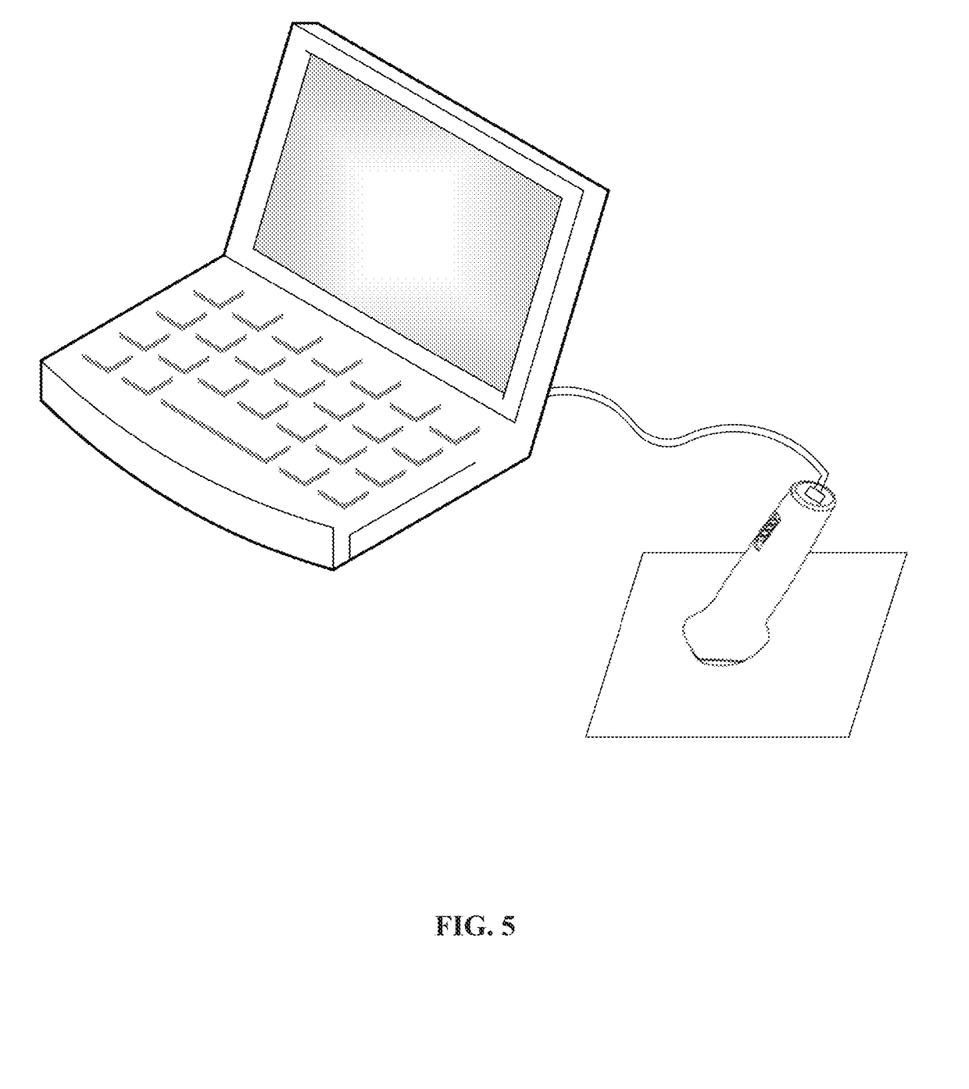
FIG. 5 illustrates a schematic diagram of a hand-held device operating on a mouse pad according to some embodiments of the present disclosure.
Figure 6:
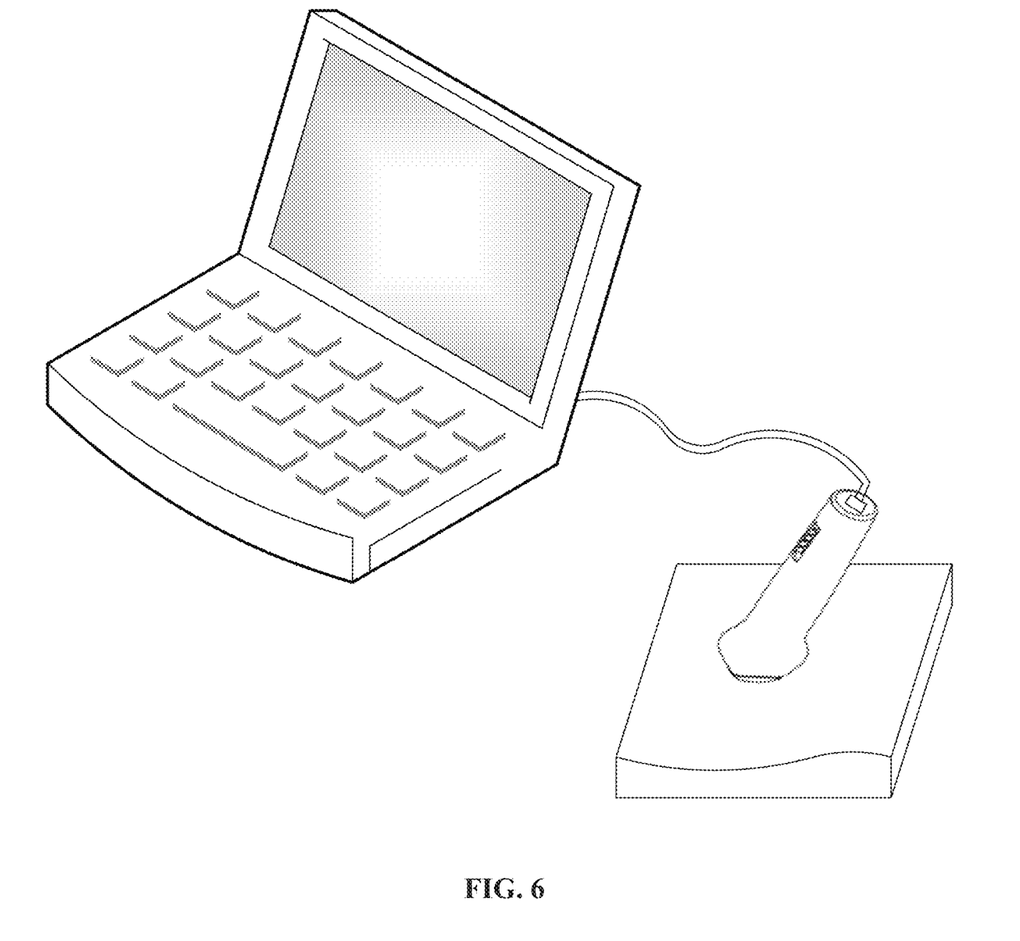
FIG. 6 illustrates a schematic diagram of a hand-held device operating on a human skin model surface according to some embodiments of the present disclosure.
Figure 7:
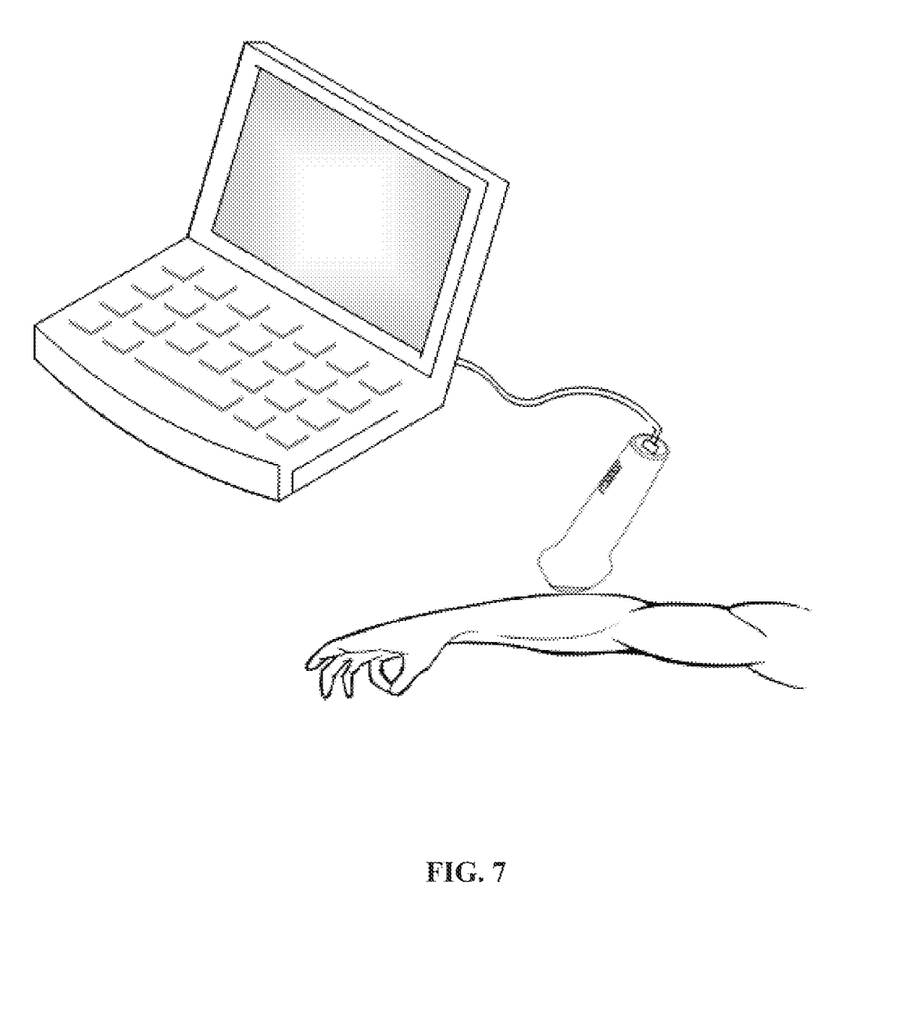
FIG. 7 illustrates a schematic diagram of a hand-held device operating on a human skin surface according to some embodiments of the present disclosure.

FIG. 5 illustrates a schematic diagram of a hand-held device operating on a mouse pad according to some embodiments of the present disclosure. FIG. 6 illustrates a schematic diagram of a hand-held device operating on a human skin model surface according to some embodiments of the present disclosure. FIG. 7 illustrates a schematic diagram of a hand-held device operating on a human skin surface according to some embodiments of the present disclosure.

Teleoperation refer to a technique configured to remotely control a system or a device. As shown in FIGS. 5-7, during the teleoperation, a doctor holds the hand-held device to perform a planar movement on the working surface, and holds the hand-held device to rotate in space. FIG. 5 illustrates that the hand-held device performs a planar movement on a mouse pad. FIG. 6 illustrates that the hand-held device performs a planar movement on the human skin model surface. FIG. 7 illustrates that the hand-held device performs a planar movement on the human skin surface. The hand-held device maps the velocity information of the hand-held device moving on the working surface, the angular velocity information of rotating in space, and the pressing force of the hand-held device to the end-effector of the sub-terminal scanning examination robot through the main computer, and performs velocity controls in a Cartesian space on the posture movement of ultrasound probe of the end-effector of the sub-terminal scanning examination robot in space and the movement of the end-effector of the sub-terminal scanning examination robot in the horizontal plane, to achieve a real-time reproduction of the ultrasound probe on the end of the sub-terminal scanning examination robot completing an action of the hand-held device.

In some embodiments, the doctor remotely controls the sub-terminal scanning examination robot by holding the hand-held device by performing the following operations.

S1, when the ultrasound probe on the end of the sub-terminal scanning examination robot is relatively far above the human body, the doctor holds the hand-held device and long-presses or clicks the up-down movement control key to control the end-effector of the sub-terminal scanning examination robot to move the end-effector downwardly along the normal direction of the scanning surface by a set distance. When the ultrasound probe on the end of the sub-terminal scanning examination robot is relatively close above the human body, the up-down movement control key is released.

S2, the doctor places the hand-held device on the working surface, the hand-held device moves on the working surface, and the hand-held device maps the velocity information moving on the working surface to the sub-terminal scanning examination robot, so that the velocity of the end-effector of the sub-terminal scanning examination robot moving on the working surface is the same as the velocity of the hand-held device moving on the working surface, to control the movement of the end-effector of the sub-terminal scanning examination robot on the horizontal plane, and adjust the ultrasound probe on the end of the sub-terminal scanning examination robot to be located above the scanning portion of the human body.

S3, the doctor long-presses the posture control key and holds the hand-held device to rotate in space, the hand-held device maps the angular velocity of the hand-held rotating in space to the sub-terminal scanning examination robot, so that the angular velocity of the end-effector of the sub-terminal scanning examination robot rotating in space is the same as the angular velocity of the hand-held device rotating in space, so that the posture movement of the end-effector of the sub-terminal scanning examination robot in space is controlled, and the ultrasound probe on the end of the sub-terminal scanning examination robot is adjusted to align with the scanning portion of the human body. When the ultrasound probe on the end of the sub-terminal scanning examination robot is aligned with scanning portion of the human body, the posture control key is released;

S4, the doctor places the hand-held device on the working surface, and at the same time applies pressure to the outer surface of the end cover 9 of the hand-held device, to generate the pressing force of the hand-held device. At this time, the doctor clicks the pressing force control key, and the hand-held device maps the pressing force to the end-effector of the sub-terminal scanning examination robot, and controls a downward movement of the end-effector of the sub-terminal scanning examination robot along a vertical direction automatically. When the contact force between the ultrasound probe at the end of the sub-terminal scanning examination robot and the human body, i.e., the actual contact force of the ultrasound probe, reaches the pressing force of the hand-held device, the end-effector of the sub-terminal scanning examination robot automatically stops the downward movement along the normal direction of the scanning surface, at this time, the ultrasound probe on the end of the sub-terminal scanning examination robot contacts the scanning portion of the human body, and the ultrasound probe may perform an ultrasound scanning on the scanning portion of the human body.

S5, the doctor places the hand-held device on the working surface, the hand-held device moves on the working surface, maps velocity information of the hand-held device moving on the working surface to the end-effector of the sub-terminal scanning examination robot, so as to control the movement of the end-effector of the sub-terminal scanning examination robot on the horizontal plane, and control the ultrasound probe on the end of the sub-terminal scanning examination robot to perform the scanning on the scanning portion of the human body. If an angle is not appropriate, the doctor may long-press the posture control key again and hold the hand-held device to rotate in space to control the posture movement of the end-effector of the sub-terminal scanning examination robot in space and adjust the ultrasound probe on the end of the sub-terminal scanning examination robot to align with the scanning portion human body. Since the surface of the human body is a concave-convex surface, the doctor may choose to press the force control key, and when the ultrasound probe on the end of the sub-terminal scanning examination robot moves on the scanning portion, an actual location of the ultrasound probe follows the human skin surface for ups and downs. Alternatively, the doctor may choose to press the up-down movement control key, and the ultrasound probe is adjusted to move along the normal surface of the scanning surface by the set distance.

In some embodiments of the present disclosure, the hand-held device adopts an integrated design, and may be connected to a computer to constitute a doctor end, i.e., a main end device. The hand-held has a simple structure and is easy to carry, and is convenient for performing an ultrasound scanning on patients in a home environment.

In some embodiments of the present disclosure, the hand-held device may be operated on any working surface, such as a desktop, a mouse pad, the human skin model surface, or the human skin surface, etc., without a need for other auxiliary devices such as a touching table. The velocity information of the hand-held device moving on the working surface is obtained directly through the photoelectric velocity sensor inside the hand-held device, and the velocity information may be configured to realize the control of the movement of the end-effector of the robotic arm on the horizontal surface.

In some embodiments of the present disclosure, the display displays in real time the pressing force of the hand-held device, the actual contact force of the ultrasound probe, and a difference between the two forces, which allows the doctor to observe the two forces more intuitively, and facilitates the doctor to clearly know the difference between the two forces, so that the doctor may know a tracking error of the actual contact force on the pressing force and obtain a force feedback, which facilitates the doctor to timely adjust the pressing force of the hand-held device.

In some embodiments of the present disclosure, the vibration module of the present disclosure generates the vibration according to the difference between the pressing force of the hand-held device and the actual contact force of the ultrasound probe. If the difference is greater than a certain set threshold, the vibration module generates the vibration, and the greater the difference is, the greater the vibration intensity of the vibration is. In the present disclosure, the vibration module generates the vibrations of different intensities according to the difference between the pressing force and the actual contact force, and form force feedback, which facilitates the doctor to timely adjust the pressing force of the hand-held device.

In some embodiments of the present disclosure, the hand-held device of the present disclosure controls the end-effector of the sub-terminal scanning examination robot to automatically move along the normal direction along the scanning surface using the pressing force, thereby ensuring a continuity of the contact force between the ultrasound probe and the human body.

In some embodiments of the present disclosure, the hand-held device of the present disclosure controls the movement of the end-effector of the sub-terminal scanning examination robot on a horizontal plane and the posture movement of the end-effector of the sub-terminal scanning examination robot in space by using the velocity information of the hand-held device moving on the working surface and the angular velocity information of the hand-held device rotating in space, which ensures the continuity of the entire movement process of the sub-terminal scanning examination robot using the velocity mapping way.

In some embodiments of the present disclosure, the hand-held device of the present disclosure switches modes through control modes, which improves an effectiveness of use and facilitates the doctor to operate.

In some embodiments of the present disclosure, the doctor holds the hand-held device to move on any working surface, the end cover 9 of the hand-held device are subjected to a pressing force, and a reaction force of the pressing force is directly fed back to the doctor. That is, when the doctor holds the ultrasound probe to move on the human skin surface, the doctor may directly sense the pressing force of the ultrasound probe to the human body without the aid of any mechanical structure or motor structure. The pressing force subjected by the end cover 9 may be used as a feedback force, so that the doctor may sense the pressing force of the ultrasound probe on the human body, and the doctor may sense a timely and efficient force sense.

In some embodiments, there is no need to provide the feedback force for the doctor through the mechanical mechanism or the motor structure, so that the hand-held device has enough space, and the velocity collection module and the force feedback module are integrated into the hand-held device, which makes the hand-held device have an integrated structure, thereby improving portability and convenience of the hand-held device, making the doctor not to be limited by an operation space, and being able to work on any working surface.

In some embodiments, the data processing module 7 in the hand-held device is further configured to obtain a desired recommended pressing force through a pressing force determination model according to the ultrasound image obtained by current ultrasound scanning and transmits the desired recommended pressing force to the doctor. The ultrasound image refers to a visualized image that is captured by the ultrasound probe and processed by a Doppler ultrasound device. The pressing force determination model is a machine learning model, and the pressing force determination model may be pre-stored in the data processing module 7.

In some embodiments, the pressing force determination model may include a deep neural network (DNN) model, a convolutional neural network models (CNN), or other customized model structures, or the like, or any combination thereof.

In some embodiments, an input of the pressing force determination model may include the ultrasound scanning image during the ultrasound scanning, and the actual pressing force of the ultrasound probe. The actual pressing force of the ultrasound probe may be obtained from the sensor of the sub-terminal scanning examination robot.

In some embodiments, the pressing force determination model may be obtained by training based on a large number of first training samples with first labels. A first training sample is ultrasound scanning image, the first label may be the actual pressing force when the ultrasound probe corresponding to the first training sample is scanned, and the first label may be obtained by collecting the pressing force when a professional ultrasound doctor is scanning.

In some embodiments of the present disclosure, the data processing module 7 obtains the ultrasound image of a current scanning portion, and the desired recommended pressing force of the current scanning portion through is obtained by the trained pressing force determination model. In some embodiments, the data processing module 7 may display the determined desired recommended pressing force to the doctor in real time through the display 6, to help the doctor to adjust a current scanning contact force according to the desired recommended pressing force to obtain an accurate ultrasound scanning image, thereby improving the working efficiency of the ultrasound scanning.

In some embodiments, the main computer may send prompting information to a doctor based on a detection result obtained through a couplant detection method. For example, the prompting information may include information indicating that the couplant of the one or more scanning points are inadequate. An exemplary couplant detection method may include an ultrasound image-based confidence detection method.

In some embodiments, during the scanning process, a real-time detection of an application of the couplant is performed based on a confidence detection of the ultrasound image. Based on the detection result, it may be determined whether the scanning is a normal scanning or the couplant needs to be added, and the operations are as follows.

In operation 1, an ultrasound image is obtained in real time, the ultrasound image is divided vertically into left and right regions evenly from the middle, and image confidence degrees of the left and right regions are determined.

In operation 2-1, when the image confidence degrees of the left and right regions are less than a set threshold, it is determined that there are black regions in left and right regions of the ultrasound image at this time, the quality of the ultrasound image is poor, and at this time, a frictional force and a scanning force in a direction of a scanning tangent are obtained through the force sensor. In operation 2-1-1, when the frictional force in the direction of the scanning tangent is less than the threshold and the scanning force is less than a maximum safe scanning force, the scanning force is increased, and operation 1 is returned to be performed. In operation 2-1-2, when the frictional force in the direction of the scanning tangent is greater than the threshold or the scanning force is greater than the maximum safe scanning force, an insufficiency of the couplant is prompted, the application of the couplant is required to perform, and operation 1 is returned to be performed.

In operation 2-2, when only one of the image confidence degrees of the left and right regions is less than the threshold, it is determined that there is a black region in the region whose the image confidence degree is less than the threshold, and the ultrasound probe is not tightly attached to the skin on this region, such that a mechanical arm is controlled to adjust the posture of the ultrasound probe, the ultrasound probe is rotated to the region whose the image confidence degree is less than the threshold, and operation 1 is returned to be performed;

In operation 2-3, when the image confidence degrees of the left and right regions are greater than the threshold, the normal scanning is performed.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure, or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures, or characteristics may be combined as suitable in one or more embodiments of the present disclosure.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting effect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Therefore, by way of example, but not of limitation, alternative configurations of the embodiments of the application may be utilized in accordance with the teachings herein. Accordingly, embodiments of the present application are not limited to that precisely as shown and described.

What is claimed is:

1. A portable teleoperation hand-held device for remote ultrasound examination, wherein the hand-held device comprises a housing, a velocity collection module disposed on the housing, an angular velocity collection module disposed on the housing, a force collection module disposed on the housing, a data processing microcontroller disposed on the housing, a pressing module disposed on the housing, and a force feedback module disposed on the housing; wherein the velocity collection module is configured to obtain velocity information of the hand-held device moving on a working surface;

the angular velocity collection module at least includes a posture angular velocity sensor and is configured to obtain angular velocity information of the hand-held device rotating in space; and the angular velocity collection module is fixed to an angular velocity collection module fixing plate disposed on the housing by a nut to ensure that when the hand-held device is rotated in space, the angular velocity collection module is capable of collecting the angular velocity information;

the force collection module at least includes a force sensor and a data transmitter and is connected to the pressing module, and is configured to obtain a pressing force to which the pressing module is subjected, the pressing force to which the pressing module is subjected being a pressing force of the hand-held device;

the velocity collection module, the angular velocity collection module, and the force collection module are all connected to the data processing microcontroller, which respectively sends the velocity information of the hand-held device moving on the working surface, the angular velocity information of the hand-held device rotating in space, and the pressing force of the hand-held device to the data processing microcontroller, and sends the velocity information of the hand-held device moving on the working surface, the angular velocity information of the hand-held device rotating in space, and the pressing force of the hand-held device to a sub-terminal scanning examination robot through the data processing microcontroller, to realize a remote control of the sub-terminal scanning examination robot;

the data processing microcontroller is further configured to receive an actual contact force between an ultrasound probe on an end of the sub-terminal scanning examination robot and a scanning portion of a human body, and send the actual contact force of the ultrasound probe to the force feedback module;

the force feedback module is configured to provide real-time feedback on the actual contact force of the ultrasound probe;

the hand-held device moves on the working surface, and the working surface is any working surface; the hand-held device is an imitation ultrasound probe, the pressing module includes an end cover disposed on one end of the housing, and an outer surface of the end cover is a pressing surface of the hand-held device;

the velocity collection module includes a photoelectric velocity sensor, a velocity detection window is opened on the outer surface of the end cover, that is, and on the pressing surface of the hand-held device, and a photoelectric detecting end of the photoelectric velocity sensor performs a photoelectric detection through the velocity detection window to obtain the velocity information of the hand-held device moving on the working surface;

the force feedback module includes a display; the display is connected to the data processing microcontroller to obtain the pressing force of the hand-held device and the actual contact force of the ultrasound probe; the display is configured to display in real time the pressing force of the hand-held device, the actual contact force of the ultrasound probe, and a difference between the pressing force of the hand-held device and the actual contact force of the ultrasound probe;

the force feedback module is further configured to obtain the difference between the pressing force of the hand-held device and the actual contact force of the ultrasound probe, generate a vibration according to the difference if the difference is greater than a set threshold, and the greater the difference is, the greater a vibration intensity of the vibration is.

2. The portable teleoperation hand-held device for remote ultrasound examination of claim 1, wherein the any working surface is a human skin model surface or a human skin surface.

3. The portable teleoperation hand-held device for remote ultrasound examination of claim 1, wherein the hand-held device is provided with a USB interface, the USB interface is used for power supply; and the data processing microcontroller transmits data through the USB interface.

4. The portable teleoperation hand-held device for remote ultrasound examination of claim 1, wherein the hand-held device controls a movement of an end-effector of the sub-terminal scanning examination robot in a horizontal plane using the velocity information of the hand-held device moving on the working surface, and the hand-held device controls a posture movement of the end-effector of the sub-terminal scanning examination robot in space using the angular velocity information of the hand-held device rotating in space.

5. The portable teleoperation hand-held device for remote ultrasound examination of claim 1, wherein the hand-held device controls the end-effector of the sub-terminal scanning examination robot to move along a normal direction of the scanning surface using the pressing force, so that the actual contact force between the ultrasound probe on the end of the sub-terminal scanning examination robot and a scanning portion of the human body, reaches the pressing force of the hand-held device.

6. The portable teleoperation hand-held device for remote ultrasound examination of claim 1, wherein the hand-held device further includes a control module;

the control module is configured to perform a mode selection, the mode including a force control mode, a posture control mode; the control module includes a force control key, a posture control key, or an up-down movement control key; the control module is connected with the data processing microcontroller, the control module sends a selected mode to the sub-terminal scanning examination robot through the data processing microcontroller to control the end-effector of the sub-terminal scanning examination robot to move in the selected mode; wherein in the force control mode, the end-effector of the sub-terminal scanning examination robot is controlled to move automatically along the normal direction of the scanning surface, so that the contact force between the ultrasound probe on the end of the sub-terminal scanning examination robot and the scanning portion of the human body, that is, the actual contact force of the ultrasound probe, reaches to the pressing force of the hand-held device; and in the posture control mode, the posture movement of the end-effector of the sub-terminal scanning examination robot in space is controlled, so that an angular velocity of the end-effector of the sub-terminal scanning examination robot rotating in space is the same as an angular velocity of the hand-held device rotating in space.

* * * * *